United States Patent [19]

Posner

[11] Patent Number: 5,645,826
[45] Date of Patent: Jul. 8, 1997

[54] METHOD OF TREATING DAMAGED TISSUE WITH SEMI-OCCLUSIVE SALICYLIC ACID OINTMENT

[75] Inventor: Robert M. Posner, Merrick, N.Y.

[73] Assignee: Abbe Cosmetic Group International, Inc., Farmingdale, N.Y.

[21] Appl. No.: 657,838

[22] Filed: May 31, 1996

Related U.S. Application Data

[63] Continuation-in-part of Ser. No. 570,997, Dec. 12, 1995, abandoned.

[60] Provisional application No. 60/007,547, Nov. 27, 1995.

[51] Int. Cl.$^6$ ................................................ A61K 31/74
[52] U.S. Cl. .................. 424/78.02; 514/865; 514/871; 514/882; 514/969
[58] Field of Search ............... 424/78.02; 514/871, 514/865, 882, 969

[56] References Cited

U.S. PATENT DOCUMENTS

| 4,219,548 | 8/1980 | Reller | 514/786 |
| 5,208,012 | 5/1993 | Sudo et al. | 424/59 |
| 5,296,476 | 3/1994 | Henderson | 514/163 |
| 5,346,886 | 9/1994 | Lezdey et al. | 514/8 |
| 5,460,620 | 10/1995 | Smith et al. | 604/290 |
| 5,482,710 | 1/1996 | Slavtcheff et al. | 424/195.1 |

*Primary Examiner*—John W. Rollins
*Assistant Examiner*—Christopher R. Tate
*Attorney, Agent, or Firm*—Jordan and Hamburg

[57] ABSTRACT

A method of treating damaged tissue by applying a composition to the damaged tissue in an amount effective to treat the damaged tissue. The composition includes a semi-occlusive ointment base and salicylic acid in an amount effective to produce keratoplasticity.

44 Claims, No Drawings

METHOD OF TREATING DAMAGED TISSUE WITH SEMI-OCCLUSIVE SALICYLIC ACID OINTMENT

CROSS REFERENCE TO RELATED APPLICATIONS

This application claims the benefit of U.S. provisional application Ser. No. 60/007,547, filed on Nov. 27, 1995, entitled METHOD OF TREATING DAMAGED TISSUE. Additionally, this application is a Continuation-in-Part of application Ser. No. 08/570,997 filed Dec. 12, 1995, now abandoned.

BACKGROUND OF THE INVENTION

The present invention is a method for treating damaged skin or other tissue, for example, burns, hemorrhoids, diaper dermatitis (diaper rash), etc. and skin and tissue subjected to laser treatment. The method applies a composition to the affected area.

The inventive method increases the rate at which damaged tissue heals. One way the method operates is by aiding in forming a bed of granulation tissue. Another aspect of the method of the invention is its use of a composition which is an ointment, which is not totally occlusive, but semi-occlusive, and allows the skin to breathe.

Hemorrhoid treatments using an ointment base do not realize the importance of ensuring the base is semi-occlusive. For example, Williams U.S. Pat. No. 4,118,480, merely refers to an ointment base of lanolin and petrolatum, without requiring that the base be semi-occlusive. Further, both Crosby, U.S. Pat. No. 4,613,498, and Gros, U.S. Pat. No. 4,626,433, use a petroleum jelly base, which, like Vaseline®, may be occlusive and may not allow the skin to breathe.

The method of the invention uses a composition including salicylic acid to produce keratoplasticity, which aids in forming a bed of granulation tissue. Reller, U.S. Pat. No. 4,126,681, uses acetyl salicylic acid as an anti-inflammatory agent and for treating burn tissue. In Reller, acetyl salicylic acid makes up to about 10% by weight of the composition when used to treat burn tissue, far more than necessary to produce keratoplasticity.

Salicylic acid derivatives are used in Reller, U.S. Pat. No. 4,199,566, in analgesic and anti-inflammatory compositions. One problem in using such a composition to heal damaged tissue is that Reller refers to using the composition in the form of a cream. Unlike the ointment based composition used in the inventive method, a cream would not be effective in the present invention, since a cream can cause further drying of tissue, thus preventing proper healing.

Jacquet, U.S. Pat. No. 4,767,750, uses salicylic acid derivatives which are more effective at producing keratolysis at lower concentrations than salicylic acid. See column 1, lines 50–55. The amount of salicylic acid used in the composition of the present invention is effective to create keratoplasticity. The amount of salicylic acid necessary to create keratoplasticity is less than that required to cause keratolysis. Since Jacquet would require less of its salicylic acid derivatives to produce keratolysis than would be required if salicylic acid were used, it may be difficult to use Jacquet's salicylic acid derivatives to create keratoplasticity.

Further, the Jacquet composition may be in the form of a cream. The composition used in the method of the present invention is not a cream, since a cream can cause further drying of tissue and is quickly absorbed into the skin where it cannot act as a protective barrier.

Tocopherols have been used in an anti-inflammatory composition to treat hemorrhoids, see Massé, U.S. Pat. No. 5,002,767, which uses a cream. Vitamin E has been used for this purpose as well, see Haimowitz, U.S. Pat. No. 4,169,143. This free radical scavenger has also been used in a sunscreen to prevent and treat sunburn, see Perricone, U.S. Pat. No. 5,376,361, which uses a cream.

No composition is known for treating damaged skin or other tissue which has semi-occlusive ointment base, allowing the skin to breathe so it can heal, and further has an amount of salicylic acid effective to produce keratoplasticity.

SUMMARY OF THE INVENTION

To address a deficiency in the prior art, the composition used in the method of the present invention has a semi-occlusive ointment base and an amount of salicylic acid effective to produce keratoplasticity. In the inventive method, a clinically, pharmaceutically and/or therapeutically effective amount of the composition is applied to the damaged area to heal it.

The above and other objects, features and advantages of the invention will become readily apparent from the following detailed description thereof.

DETAILED DESCRIPTION OF THE INVENTION

The composition used in the method of the claimed invention includes an ointment base and salicylic acid. The ointment base must allow the skin to breathe, i.e., it cannot be totally occlusive. It is preferable to include one or more free radical scavengers and therapeutic agents in the composition as well.

A preferred ointment base is a petrolatum and lanolin base. The petrolatum and lanolin base is semi-occlusive (semi-permeable) which allows the skin to breath. Vaseline®, for example, is totally occlusive, and will not allow the skin to breathe. It is important to allow the skin to breathe so it can heal. When the skin cannot breathe it macerates and will break down. The ratio of lanolin to petrolatum can affect the semi-occlusivity of the composition. Preferably, the ratio of lanolin to petrolatum is 3:5.

In some situations it may be preferable to use a softer, more pliable ointment, such as for sensitive skin. One way to make the ointment softer and more pliable is by altering the ointment base to include more petrolatum and less lanolin than the ointment base disclosed in the preceding paragraph.

The ointment base forms a protectant on the skin, but still allows the skin to respirate. The composition does not use a cream base; a cream base would not be effective, since cream vanishes and gets absorbed by the skin and then it no longer acts as a protectant.

In the composition, yellow or amber petrolatum (also referred to as yellow/amber petrolatum) is preferred, but white petrolatum or other color gradations between white and yellow/amber petrolatum could be used. The petrolatum is preferably used in a range of about 35 to about 70% by weight of the total composition. A more preferred range is about 40 to about 60%. An even more preferred range is about 50 to about 55%. All amounts herein are by weight.

A greater amount of petrolatum, such as a range from about 70 to about 95%, can be used to prepare a softer, more pliable ointment. The petrolatum can also be used in a range of about 75 to about 90% or a range of about 80 to about 85%.

The lanolin is preferably used in an amount of about 15 to about 40% by weight. A more preferred range is about 20 to about 35%. The amount of lanolin used to prepare a softer, more pliable ointment, which is preferable for more sensitive skin, is about 2 to about 10% by weight. A more preferred range is about 4 to about 7% by weight.

It is preferable that the lanolin be anhydrous to more easily form a semi-occlusive base with the petrolatum. It is also preferable to use anhydrous lanolin from which insecticides have been removed. An example of this type of lanolin is LP 108 manufactured by Amerchol Company.

The preferred salicylic acid is salicylic acid USP. The amount of salicylic acid used is that which produces keratoplasticity, stimulating fibroblastic activity at the granular cell level to produce tropocollagen at a more rapid rate. The dosage of salicylic acid is preferably set so that it does not create keratolysis. As a result of using salicylic acid, the method of the invention produces more movement of the cells at the basal cell layer of the affected skin or tissue to grow more cells, which is keratoplasticity. The method of the invention is not concerned with sloughing off cells, which is keratolysis.

The amount of salicylic acid is adjusted as stated above to produce keratoplasticity. A preferred range of salicylic acid is about 0.005 to about 5.0%. A more preferred range is about 0.01 to about 3.0%. An even more preferable range is about 0.05 to about 0.1%.

In a preferred embodiment of the inventive method, the amount of salicylic acid used is enough to induce keratoplasticity, but is not enough to cause keratolysis.

One preferred free radical scavenger and therapeutic agent is Vitamin E, a therapeutic agent which prevents hypertrophic scarring and acts as a free radical scavenger. Any form of Vitamin E can be used, whether or not separated from other tocopherols. Examples of types of Vitamin E include Vitamin E acetate, Vitamin E palmitate and Vitamin E linoleate. It is preferable to use Vitamin E acetate.

The vitamin E, which is a slightly viscous oil, affects the physical characteristics of the base in a preferable manner.

Other preferred free radical scavengers and therapeutic agents include any form of Vitamin C, any form of Vitamin A, superoxide dismutase, beta carotene, etc. One example of a form of Vitamin C is ascorbyl palmitate.

The free radical scavengers referred to above are preferably used in a range of about 0.5 to about 5.0%. A more preferred range is about 1.0 to about 4.0%.

It is preferable that the free radical scavenger(s) used is oil soluble or made to be oil soluble.

Extracts from the balsam tree of Peru can also be used as therapeutic agents. Examples of such extracts include benzyl cinnamate and aldehyde C-16. Preferred ranges of each of these agents are about 0.25 to about 1.5%, and more preferably about 0.5 to about 1.0%.

It is also preferable to use a wax in the composition. It helps to stiffen the composition, make it harder, and to aid in making it semi-occlusive. Examples of the wax include cetyl esters wax, ozokerite wax, paraffin wax and natural spermaceti. A single wax or a combination of different waxes can be used. It is preferable to use the NF grade of cetyl esters wax.

In a preferred embodiment, about 1.0 to about 4.0% of the wax is used, and more preferably about 2.0 to about 3.0% is used.

The wax is optimally not included in the softer, more elastic ointment composition, since, as noted, the wax makes the composition harder.

The method of the present invention applies the disclosed composition to the affected area. For example, the composition may be applied topically. When the method is used to treat hemorrhoids, the composition may be placed in a conventional suppository which melts at body temperature, or it may be applied directly as an ointment.

An amount of the composition effective to treat the damaged area is applied until the area is healed. For topical application, a conventional amount of the composition is used. For example, a dab on the finger is applied once a day as required to cover the affected area, as with bacitracin or PREPARATION H®. Preferably, the composition is applied 2 to 3 times a day.

EXAMPLES

In an example of a method to produce the composition used in the present invention, the components of the composition are weighed separately and then mixed together and heated to form the composition. Preferably, the yellow/amber petrolatum is first weighed and then the anhydrous lanolin is weighed and added to the petrolatum to form a mixture. The Vitamin E acetate is then weighed and added to the mixture, then the cetyl esters wax, the benzyl cinnamate, the aldehyde C-16 and the salicylic acid are each weighed and consecutively added to the mixture. The whole mixture is heated to a temperature in the range of about 75° C. to about 80° C. while mixing. The mixture is to be filled at a temperature between about 60° C. and about 70° C., and cooled in a cooling tunnel or by ambient air.

Example 1

An example of the composition produced by the above method includes 57.95% yellow/amber petrolatum, 35% anhydrous lanolin, 0.05% salicylic acid, 4.0% Vitamin E acetate, 0.5% benzyl cinnamate, 0.5% aldehyde C-16 and 2.0% cetyl esters wax. All percentages are by weight.

Once the composition is formed, it is applied to the affected area. For example, when the skin damage is due to sunburn, the composition is topically applied to the burnt area to speed healing thereof.

In the method of the present invention, the composition used is applied as often as needed to speed the healing process in a beneficial manner which avoids scarring of the tissue.

Example 2

The composition of Example 1 was applied to a first degree burn received from a hot stove. Within twenty minutes after the first application of the composition, the pain caused by the burn was completely gone. The composition was applied a total of three times on the day the burn was received at an interval of approximately 3–4 hours between each application. The composition was effective to completely heal the burn after the first day of use.

Example 3

The composition of Example 1 was applied to a second degree burn received from a hot stove. Within twenty minutes after the first application of the composition, the pain caused by the burn was completely gone. The composition was applied three times a day, on the day the burn was received and on the following two days, at an interval of approximately 3–4 hours between each application. The composition was effective to substantially heal the burn after the third day of use.

Example 4

The composition of Example 1 was topically applied to hemorrhoids. Within twenty minutes of the first application of the composition, the itching and burning symptoms of the hemorrhoids had subsided. The composition was applied a total of three times on the day of the first application and the hemorrhoids receded overnight.

Example 5

The composition of claim 1 was applied to ammoniacal diaper dermatitis. In this type of diaper dermatitis, the urine breaks down to ammonia between diaper changes and causes a rash. Application of the composition operates to clear up the rash and form a protective barrier on the skin so that urine cannot contact the skin which is protected. The protective barrier was formed upon the first application of the composition. The rash was cleared up following two applications of the composition, including the first application of the composition which formed the protective barrier. The second application occurred three hours after the first. Subsequent applications upon each diaper change allowed the protective barrier to reform.

Example 6

Another example of a composition produced by a method the same as that used in Example 1, but which does not contain a wax, includes 89.95% yellow/amber petrolatum, 5% anhydrous lanolin, 0.05% salicylic acid, 4.0% Vitamin E acetate, 0.5% benzyl cinnamate, and 0.5% aldehyde C-16. All percentages are by weight.

The composition of Example 6 is applied to the affected area as often as needed to speed the healing process in a beneficial manner which avoids scarring of the tissue.

Example 7

The composition of Example 6 was applied to sensitive skin subjected to laser therapy. The skin treated with the composition was soothed and healed faster as a result of one topical application of the composition. The composition was applied twice a day for two days, to heal the skin faster than conventional post-laser therapy treatments and to simultaneously avoid scarring.

Example 8

The composition of Example 6 was topically applied to sensitive skin subjected to laser treatment. This post-laser therapy was continued twice a day for three days. The composition of Example 1 was applied to the laser treated skin the fourth and fifth day after laser therapy, once the extra sensitivity of the treated skin subsided. The inventive post-laser therapy treatment of the present example healed the skin faster than conventional treatments and avoided scarring at the same time.

The present invention is also concerned with a method of conditioning leather and vinyl and stimulating the coronet band of horses's hooves by applying a composition thereto in an amount conventionally used and effective for the purpose.

Having described the present invention, it should be appreciated that the present invention is not limited to the examples described, in that various changes and modifications can be effected therein by one of ordinary skill in the art without departing from the scope of the invention as defined by the appended claims.

I claim:

1. A method of treating damaged tissue comprising applying a pharmaceutically effective amount of a composition to damaged tissue, the composition comprising a semi-occlusive ointment base and salicylic acid in an amount effective to produce keratoplasticity and ineffective to cause keratolysis, the ointment base being yellow/amber petrolatum and anhydrous lanolin.

2. The method of claim 1, wherein the composition further comprises at least one free radical scavenger selected from the group consisting of vitamin E, vitamin A, vitamin C and beta carotene, and at least one therapeutic agent selected from the group consisting of benzyl cinnamate and aldehyde C-16.

3. The method of claim 1, wherein a pharmaceutically effective amount of the composition effective for treating damaged tissue is applied once a day.

4. The method of claim 1, wherein a pharmaceutically effective amount of the composition effective for treating damaged tissue is applied two to three times a day.

5. The method of claim 1, wherein the mode of application is topical.

6. The method of claim 1, wherein the composition is applied using a suppository, containing the composition, which melts at body temperature.

7. The method of claim 1, wherein the damaged tissue treated is one selected from the group consisting of burns, hemorrhoids and diaper dermatitis.

8. The method of claim 1, wherein the composition is applied for a predetermined amount of time and further comprising applying another composition after the predetermined amount of time has passed, the other composition comprising about 0.05 to about 0.1 wt % salicylic acid, about 40 to about 60 wt % yellow/amber petrolalum, about 20 to about 35 wt % anhydrous lanolin, about 1.0 to about 4.0 wt % vitamin E, about 0.5 to about 1.0 wt % benzyl cinnamate, about 0.5 to about 1.0 wt % aldehyde C-16, and about 2.0 to about 3.0 wt % cetyl esters wax.

9. The method of claim 1, wherein the amount of salicylic acid is about 0.05 to about 0.1 wt %, the yellow/amber petrolatum is present in an amount of about 40 to about 60 wt %, the anhydrous lanolin is present in an amount of about 20 to about 35 wt %, and the composition further comprises vitamin E in an amount of about 1.0 to about 4.0 wt %, benzyl cinnamate and aldehyde C-16, each of which is present in an amount of about 0.5 to about 1.0 wt %, and cetyl esters wax in an amount of about 2.0 to about 3.0 wt %.

10. A method of treating damaged tissue comprising applying a pharmaceutically effective amount of a composition to damaged tissue, the composition comprising a semi-occlusive ointment base and salicylic acid in an amount effective to produce keratoplasticity and ineffective to cause keratolysis, the ointment base being lanolin and petrolatum, and the ratio of lanolin to petrolatum being 3:5.

11. The method of claim 10, wherein the composition further comprises at least one free radical scavenger selected from the group consisting of vitamin E, vitamin A, vitamin C and beta carotene, and at least one therapeutic agent selected from the group consisting of benzyl cinnamate and aldehyde C-16.

12. The method of claim 10, wherein a pharmaceutically effective amount of the composition effective for treating damaged tissue is applied once a day.

13. The method of claim 10, wherein a pharmaceutically effective amount of the composition effective for treating damaged tissue is applied two to three times a day.

14. The method of claim 10, wherein the mode of application is topical.

15. The method of claim 10, wherein the composition is applied using a suppository, containing the composition, which melts at body temperature.

16. The method of claim 10, wherein the damaged tissue treated is one selected from the group consisting of burns, hemorrhoids and diaper dermatitis.

17. The method of claim 10, wherein the composition is applied for a predetermined amount of time and further comprising applying another composition after the predetermined amount of time has passed, the other composition comprising about 0.05 to about 0.1 wt % salicylic acid, about 40 to about 60 wt % yellow/amber petrolatum, about 20 to about 35 wt % anhydrous lanolin, about 1.0 to about 4.0 wt % vitamin E, about 0.5 to about 1.0 wt % benzyl cinnamate, about 0.5 to about 1.0 wt % aldehyde C-16, and about 2.0 to about 3.0 wt % cetyl esters wax.

18. The method of claim 10, wherein the amount of salicylic acid is about 0.05 to about 0.1 wt %, the petrolatum is yellow/amber petrolatum and is present in an amount of about 40 to about 60 wt %, the lanolin is anhydrous lanolin and is present in an amount of about 20 to about 35 wt %, and the composition further comprises vitamin E in an amount of about 1.0 to about 4.0 wt %, benzyl cinnamate and aldehyde C-16, each of which is present in an amount of about 0.5 to about 1.0 wt %, and cetyl esters wax in an amount of about 2.0 to about 3.0 wt %.

19. A method of treating damaged tissue comprising applying a pharmaceutically effective amount of a composition to damaged tissue, the composition comprising a semi-occlusive ointment base and salicylic acid in an amount effective to produce keratoplasticity and ineffective to cause keratolysis, the amount of salicylic acid being 0.005–0.1% by weight.

20. The method of claim 19, wherein the composition further comprises at least one free radical scavenger selected from the group consisting of vitamin E, vitamin A, vitamin C and beta carotene, and at least one therapeutic agent selected from the group consisting of benzyl cinnamate and aldehyde C-16.

21. The method of claim 19, wherein a pharmaceutically effective amount of the composition effective for treating damaged tissue is applied once a day.

22. The method of claim 19, wherein a pharmaceutically effective amount of the composition effective for treating damaged tissue is applied two to three times a day.

23. The method of claim 19, wherein the mode of application is topical.

24. The method of claim 19, wherein the composition is applied using a suppository, containing the composition, which melts at body temperature.

25. The method of claim 19, wherein the damaged tissue treated is one selected from the group consisting of burns, hemorrhoids and diaper dermatitis.

26. The method of claim 19, wherein the composition is applied for a predetermined amount of time and further comprising applying another composition after the predetermined amount of time has passed, the other composition comprising about 0.05 to about 0.1 wt % salicylic acid, about 40 to about 60 wt % yellow/amber petrolatum, about 20 to about 35 wt % anhydrous lanolin, about 1.0 to about 4.0 wt % vitamin E, about 0.5 to about 1.0 wt % benzyl cinnamate, about 0.5 to about 1.0 wt % aldehyde C-16, and about 2.0 to about 3.0 wt % cetyl esters wax.

27. The method of claim 19, wherein the amount of salicylic acid is about 0.05 to about 0.1 wt %, the semi-occlusive ointment base is petrolatum and lanolin, the petrolatum is present in an amount of about 40 to about 60 wt %, the lanolin is present in an amount of about 20 to about 35 wt %, and the composition further comprises vitamin E in an amount of about 1.0 to about 4.0 wt %, benzyl cinnamate and aldehyde C-16, each of which is present in an amount of about 0.5 to about 1.0 wt %, and cetyl esters wax in an amount of about 2.0 to about 3.0 wt %.

28. A method of forming a bed of granulation tissue comprising applying a pharmaceutically effective amount of a composition to damaged tissue, the composition comprising a semi-occlusive ointment base of petrolatum and lanolin, salicylic acid, a free radical scavenger, a therapeutic agent and a wax, the free radical scavenger being at least one selected from the group consisting of vitamin E, vitamin A, and beta carotene, the therapeutic agent being at least one compound selected from the group consisting of benzyl cinnamate and aldehyde C-16 and the wax being at least one selected from the group consisting of cetyl esters wax, ozokerite wax, paraffin wax and spermaceti, the amount of salicylic acid being about 0.005 to about 0.1 wt %, the amount of petrolatum being about 35 to about 70 wt %, the amount of lanolin being about 15 to about 40 wt %, the amount of free radical scavenger being about 0.5 to about 5.0 wt %, the amount of the therapeutic agent being about 0.25 to about 1.5 wt %, and the amount of the wax being about 1.0 to about 4.0 wt %.

29. The method of claim 28, wherein the petrolatum is yellow/amber petrolatum and the lanolin is anhydrous lanolin.

30. The method of claim 28, wherein the amount of salicylic acid is about 0.01 to about 0.1 wt %, the amount of petrolatum is about 40 to about 60 wt %, the amount of lanolin is about 20 to about 35 wt %, the amount of free radical scavenger is about 1.0 to about 4.0 wt %, the amount of the therapeutic agent is about 0.5 to about 1.0 wt %, and the amount of the wax is about 2.0 to about 3.0 wt %.

31. The method of claim 28, wherein the amount of salicylic acid is about 0.05 to about 0.1 wt %, the amount of petrolatum is about 50 to about 55 wt %, the amount of lanolin is about 20 to about 35 wt %, the amount of free radical scavenger is about 1.0 to about 4.0 wt %, the amount of the therapeutic agent is about 0.5 to about 1.0 wt %, and the amount of the wax is about 1.0 to about 4.0 wt %.

32. The method of claim 28, wherein the amount of salicylic acid is about 0.05 to about 0.1 wt %, the petrolatum is yellow/amber petrolatum and is present in an amount of about 40 to about 60 wt %, the lanolin is anhydrous lanolin and is present in an amount of about 20 to about 35 wt %, the free radical scavenger is vitamin E and is present in an amount of about 1.0 to about 4.0 wt %, the therapeutic agent is benzyl cinnamate and aldehyde C-16, each of which is present in an amount of about 0.5 to about 1.0 wt %, and the wax is cetyl esters wax and is present in an amount of about 2.0 to about 3.0 wt %.

33. The method of claim 28, wherein the free radical scavenger is vitamin E, the therapeutic agent is benzyl cinnamate and aldehyde C-16 and the wax is cetyl esters wax.

34. The method of claim 28, wherein a pharmaceutically effective amount of the composition effective for forming a bed of granulation tissue is applied once a day.

35. The method of claim 28, wherein a pharmaceutically effective amount of the composition effective for forming a bed of granulation tissue is applied two to three times a day.

36. The method of claim 28, wherein the mode of application is topical.

37. The method of claim 28, wherein the composition is applied using a suppository, containing the composition, which melts at body temperature.

38. The method of claim 28, wherein the damaged tissue treated is one selected from the group consisting of burns, hemorrhoids and diaper dermatitis.

39. A method of treating damaged skin or other tissue comprising applying a pharmaceutically effective amount of a composition to damaged tissue, the composition comprising a semi-occlusive ointment base, salicylic acid, a free radical scavenger, and a therapeutic agent, the free radical scavenger being at least one selected from the group consisting of vitamin E, vitamin A, vitamin C and beta carotene, and the therapeutic agent being at least one compound selected from the group consisting of benzyl cinnamate and aldehyde C-16, the amount of salicylic acid being about 0.01 to about 0.1 wt %, the amount of petrolatum being about 70 to about 95 wt %, the amount of lanolin being about 4 to about 7 wt %, the amount of free radical scavenger being about 1.0 to about 4.0 wt %, and the amount of the therapeutic agent being about 0.5 to about 1.0 wt %.

40. The method of claim 39, wherein the composition is applied for a predetermined amount of time and further comprising applying another composition after the predetermined amount of time has passed, the other composition comprising about 0.05 to about 0.1 wt % salicylic acid, about 40 to about 60 wt % yellow/amber petrolatum, about 20 to about 35 wt % anhydrous lanolin, about 1.0 to about 4.0 wt % vitamin E, about 0.5 to about 1.0 wt % benzyl cinnamate, about 0.5 to about 1.0 wt % aldehyde C-16, and about 2.0 to about 3.0 wt % cetyl esters wax.

41. The method of claim 39, wherein the damaged tissue treated is one selected from the group consisting of burns, hemorrhoids, diaper dermatitis and skin and tissue subjected to laser treatment.

42. The method of claim 39, wherein a pharmaceutically effective amount of the composition effective for treating damaged tissue is applied once a day.

43. The method of claim 39, wherein a pharmaceutically effective amount of the composition effective for treating damaged tissue is applied two to three times a day.

44. The method of claim 39, wherein the mode of application is topical.

* * * * *